United States Patent [19]

Martani et al.

[11] Patent Number: 4,834,965

[45] Date of Patent: May 30, 1989

[54] CONTROLLED RELEASE PHARMACEUTICAL COMPOSITION

[75] Inventors: Rosa Martani; Elisabeth Le Huede; Jeanne Dumas, all of Bordeaux, France

[73] Assignee: Euroceltique, S.A., Luxembourg, Luxembourg

[21] Appl. No.: 119,733

[22] Filed: Nov. 12, 1987

Related U.S. Application Data

[63] Continuation of Ser. No. 888,061, Jul. 22, 1986, abandoned.

[30] Foreign Application Priority Data

Jul. 26, 1985 [FR] France .................................. 85 11575

[51] Int. Cl.$^4$ ........................ A01N 25/26; A61K 9/22
[52] U.S. Cl. ................................................. 424/488;
[58] Field of Search .................. 424/19, 22, 781, 965; 514/488

[56] References Cited

U.S. PATENT DOCUMENTS 4,540,566 9/1985 Davis et al. ........................ 424/22

Primary Examiner—Curtis R. Davis
Attorney, Agent, or Firm—Steinberg & Raskin

[57] ABSTRACT

A solid, controlled release pharmaceutical composition is provided with enhanced levels of control over drug release. The composition comprises an acid addition salt or a quarternary ammonium salt of an organic base drug complexed with an anionic surfactant and distributed in a matrix of a hydrophilic polymer. The complex formation between the drug which is preferably an acid addition salt of an organic an organic amine, and the surfactant, which is preferably a sulphosuccinate, distributed in the hydrophilic polymer matrix, which is preferably a water soluble hydroxyalkylcellulose ether results in a composition with excellent controlled released characteristics.

11 Claims, No Drawings

CONTROLLED RELEASE PHARMACEUTICAL COMPOSITION

This is a continuation of application Ser. No. 888,061, filed 7/22/86, and now abandoned.

BACKGROUND OF THE INVENTION

The use of hydrophilic polymers in the controlled release of medicaments is known. A problem with such polymers is, however, that large quantities of the hydrophilic material is often required in order to effect proper control of drug release. This is a particularly severe problem when the unit dose of the medicament is large (e.g. above about 60% by wt).

The use of anionic surfactants in solid pharmaceutical compositions is also known. Until recently, however, the presence of such surfactants was designed to facilitate fast and total release of the medicament from the composition (see, for example, Japanese Kokai 7320778 and A.A. Kassem etal, *J. Drug Research*, 1974, 6, 95).

U.S. Pat. No. 4,540,566 and P.B. Daly et al, Int. J. Pharm. 18, 201 (1984) describes a controlled release composition containing chlorpheniramine maleate, a cellulose ether and an anionic surfactant. However, the composition is a simple mixture and does not provide any particular advantages.

SUMMARY OF THE INVENTION

It is a primary object of the present invention to provide controlled release pharmaceutical compositions with improved controlled release characteristics.

It is another object of the present invention to provide controlled release pharmaceutical compositions wherein the drug, which is the acid addition salt or quarternary ammonium of an organic base, is complexed with an anionic surfactant and distributed in a hydrophilic polymer, whereby the control of drug release is considerably facilitated and made more flexible.

Other objects and advantages of the present invention will be apparent from a further reading of the specification and of the appended claims.

With the above and other objects in view, the present invention mainly comprises a complex of an acid addition salt or quarternary ammonium salt of an organic base drug and a pharmaceutically acceptable anionic surfactant distributed in a hydrophilic polymer matrix.

It has been found that the contacting of the acid addition salt or quarternary ammonium salt of the basic drug with the surfacant results in complex formation between the drug and the surfactant, with substantially all of the drug and surfactant (at least 70% by weight and up to 100% by weight of the drug) being complexed. In this form, the complex distributed in the hydrophilic polymer matrix provides excellent controlled release of the drug when injested.

Preferably the composition is in unit dosage form and administered by the oral route, especially as a tablet or as a capsule containing solid granules.

It has been found that, when the drug is an acid addition salt of an organic base or a quaternary ammonium salt complexed with the anionic surfactant an enhanced level of control over drug release is obtained. This enhanced effect is achieved by the complex formation between the acid addition salt (of the organic base) or the quaternary ammonium salt thereof and the anionic surfactant, the complex formed being water soluble at all biological pHs, especially between pH 1.5 to 7.0.

The combined use of the hydrophilic polymer and the anionic surfactant complex allows considerable flexibility in the control of drug release from compositions according to this invention. The rate of drug release, which is independent of pH, may be altered simply by modifying the polymer/surfactant in the composition, the release of a drug at any point within the digestive tract (and at any pH within the tract, 1.5 to 7.0) may be controlled).

Furthermore, the use of the anionic surfactant complex in combination with the hydrophilic polymer, allows the quantity of the polymer in the composition to be reduced without detriment to the control of the drug release. This is particularly advantageous when the composition contains a large quantity of drug. The combination (polymer/surfactant) also facilitates the compression (and shaping) of the present pharmaceutical composition into unit dosae forms.

The anionic surfactants which are effective in the present composition include alkali metal sulphates, such as sodium or potassium dodecylsulphate, sodium octadecysulphate, and, which is preferred, alkali metal sulphonates, such as the alkali metal salts of benzene sulphonates, naphthalene sulphonates and, especially, dialkysulphosuccinates. An alkali metal, especially sodium, salt of dioctylsodium sulphosuccinate is not absorbed upon oral administration.

The hydrophilic polymer may be any of the hydrophilic polymers employed in pharmaceutical compositions, especially controlled release pharmaceutical compositions. Examples include carboxyalkylcellulose, alginic acid derivatives and carboxypolymethylenes (e.g. Carbopol, Trademark). Preferably, however, the hydrophilic polymer is a water soluble, non-ionic cellulose ether, especially a hydroxyalkyl cellulose ether. Examples include hydroxymethyl cellulose, hydroxyethyl cellulose, hydroxypropyl cellulose and, which is preferred, hydroxypropyl. cellulose, and which is preferred, hydroxypropylmethyl cellulose.

Most preferably, the hydrophilic polymer, especially the cellulose ether, has a number average molecular weight of at least 50,000, especially at least 75,000.

The amount of the hydrophilic polymer and the anionic surfactant in the present composition, as well as the ratio of these materials, will depend, inter alia, on the rate of the drug release required. Preferably, the combined wt % of polymer and surfactant in the present composition is between 10% and 60%, especially between 10% and 50%. The preferred ratio (of polymer to surfactant) is between 50 to 1 and 1 to 2, especially between 30 to 1 and 1 to 1. Preferably each unit dose of the present composition contains between 1mg and 30mg, especially between 2mg and 20mg of the anionic surfactant.

In the case of dioctyl sodium sulphosuccinate, which at high levels acts as a laxative, the use of such low levels of the surfactant represents a distinct advantage.

The drug may be either any acid addition salt (inorganic or organic) of an organic base or any quaternary ammonium salt thereof. Preferably the drug is an acid addition salt of an organic amine. Examples of suitable drugs are:

(a) Analgesic agents; e.g. salts of morphine, codeine, ethyl morphine, dihydrocodeine, hydromorphone, phenazocine, pentazocine, buprenorphine, meptazinol, flupirtine, (b) Antiinflammatory agents; e.g. salts of aminopyrine, (c) Antihistamines; e.g. salts of clemastine, mepyramine, diphenlhydramine, dexchlorpheniramine,
(d) Topical anesthetics; e.g. salts of lidocaine, procaine,
(e) Vasodilators; e.g. salts of papaverine, diltiazem, nicardipine,
(f) Antitussives and expectorants, e.g. salts of isprotenerol, dextromethorphan,
(g) Antihypertensives; e.g. salts of clonidine,
(h) Antineoplastic agents; e.g. salts of doxorubicin,
(i) Bronchodilators; e.g. ipratropium bromide, and salts of albuterol (salbutamol).
(j) Antiarrythmic agents; e.g. salts of verpamil, quinidine,
(k) Antibiotics or fungicides; e.g. salts of tetracyclines, neomycine,
(l) Chemotherapeutic agents; e.g. salts of clotrimazole,
(m) Oral antiseptics; e.g. dequalinium chloride, and salts of chlordexidine, ethacridine,
(n) Anticholinergics; e.g. salts of scopolamine,
(o) Muscle relaxants; e.g. salts of baclofen, cyclobenzaprine,
(p) Drugs for treatment of ulcers; e.g. salts of cimetidine, ranitidine,
(q) Antimetics; e.g. salts of metoclopramide,
(r) Antimalarials, e.g. salts of quinine,
(s) Antipsychotics; e.g. salts of perphenazine.

Particularly preferred drugs for use in the present composition are acid addition salts of metoclopramide, codeine, ethylmorphine, morphine, dextromethorphan, quinidine, quinine, dihydrocodeine, hydromorphone, perphenazine, diltiazem, meptazinol and flupirtine, especially metoclopramide hydrochloride, codeine phosphate, ethylmorphine, hydrochloride, morphine sulphate, dextromethorphan hydrobromide, quinidine polygalacturonate, quinine sulphate, dihydrocodeine tartrate, hydromorphone hydrochloride, perphenazine hydrochloride, diltiazem hydrochloride, meptazinol hydrochloride and flupirtine maleate.

These drugs can be used either singly or as a mixture of two or more. The amount of drug to be blended in a solid dosage unit will generally be enough to maintain a therapeutic level of the drug in the bloodstream for a predetermined period (preferably 8 hours or longer).

In addition to the constituents discussed above, the present controlled release pharmaceutical composition may also contain known excipients, such as lubricants, binders, vehicles, colouring agents, taste controlling agents and odour controlling agents, that are employed to improve the appearance, odour or taste of pharmaceutical preparations.

In order to facilitate the preparation of a unit dosage form from the present composition there is provided, in a further aspect of the present invention, a process for the preparation of a solid, controlled release, pharmaceutical unit dosage form comprising granulating a composition comprising a drug, a hydrophilic polymer and an antionic surfactant and, optionally, compressing and shaping the granules wherein the drug is either an acid addition salt of an organic base or a quaternary ammonium salt.

In a particularly preferred embodiment of the present process, the anionic surfactant is dissolved in a $C_1$-$C_6$ alkyl alcohol, especially a $C_2$-$C_4$ alkyl alcohol, or in an aqueous alcoholic solution and the hydrophilic polymer is then mixed with the surfactant solution to form a homogeneous mixture. Granulation of this mixture is followed by the addition of the drug to the granules, wherein the drug and surfactant complex.

DESCRIPTION OF THE PREFERRED EMBODIMENTS

The following examples are given to further illustrate the present invention. The scope of the invention is not, however, meant to be limited to the specific details of the examples:

EXAMPLE 1

Dioctyl sodium sulphosuccinate (4.0 gm) was dissolved in isopropanol (25 ml). Hydroxpropylmethyl cellulose (90 gm, Metolose 90SH 4000) was mixed with the sulphoscuccinate solution until the mixture was homogeneous, the formation of granules being avoided. The mixtures was then granulated and sieved through a 16 mesh screen. The granules were left to dry in the air until the isopropanol had evaporated.

Quinidine polygalacturonate (288.75 gm) and lactose (32.63 gm) were then added and the whole was mixed thoroughly, resulting in complex formation between the quinidine salt and the dioctyl sodium sulphosuccinate. Magnesium stearate (0.42 gm) and talc (4.2 gm) were then added and mixing was continued until a homogeneous mixture was obtained. Finally, the mixture was regranulated and sieved through a 16 mesh screen.

The granules obtained were compressed and shaped into one thousand 420mg tablets, each containing 288.75mg of quinidine polygalacturonate.

EXAMPLE 2

The procedure of Example 1 was repeated except that the amounts of materials used were as follows:

| | |
|---|---|
| Quinidine polygalacturonate | 412.5 gm |
| Iron oxide red | 0.5 gm |
| Hydroxypropylmethyl cellulose | 92 gm |
| Dioctyl sodium sulphosuccinate | 4 gm |
| Talc | 5.8 gm |
| Magnesium Stearate | 0.58 gm |
| Lactose | 65 gm |

This produced 1,000 tablets weighing 580mg and containing 412.5mg of quinidine polygalacturonate.

EXAMPLE 3

Metoclopramide hydrochloride (15 gm was mixed with hydroxpropylmethyl cellulose (18 gm) and lactose (80.75 gm). The mixture was granulated with a solution of dioctyl sodium sulphosuccinate (7.5 gm) in isopropanol. The granules were then dried and lubricated, with talc (2.5 gm) and magnesium stearate (1.25 gm).

The granules obtained were compressed and shaped into 1000 tablets each weighing 125mg. and each containing 15mg of metoclopramide hydrochloride.

EXAMPLE 4

The procedure of Example 3 was followed except that hydroxypropylmethyl cellulose (30 gm) and dioctyl sodium sulphosuccinate (5 gm) was used. The amount of lactose was reduced to 71.25 gm. This produced 1000 tablets weighing 125mg and containing 15mg of metoclopramide hydrochloride.

EXAMPLE 5

(Comparative)

The procedure of Example 3 was followed except that no dioctyl sodium sulphosuccinate was used and the amount of hydroxypropylmethyl cellulose was increased to 42 gm. The amount of lactose was reduced to 64.25 gm.

EXAMPLE 6

The procedure of Example 3 was repeated with the following ingredients,

| | |
|---|---|
| Metoclopramide hydrochloride | 15 gm |
| Hydroxpropylmethyl cellulose | 30 gm |
| Dioctyl sodium sulphosuccinate | 12.5 gm |
| Talc | 2.5 gm |
| Magnesium stearate | 1.25 gm |
| Lactose | 63.75 gm |

This produced 1000 tablets weighing 125mg and containing 15mg of metoclopramide hydrochloride.

EXAMPLES 7-10

The procedure of Example 6 was followed except that the amount of dioctyl sodium sulphosuccinate was varied as follows:

| | Amount of Dioctyl Sodium Sulphosuccinate |
|---|---|
| Example 7 | 6.25 gm |
| Example 8 | 5 gm |
| Example 9 | 4 gm |
| Example 10 | 2 gm |

In each case, the amount of lactose was increased, as required, in order to give tablets the same weight as produced in Example 6.

EXAMPLE 11

(Comparative)

The procedure of Example 6 was repeated except that no dioctyl sodium sulphosuccinate was employed and the amount of lactose was increased by 12.5 gm.

EXAMPLE 12

The procedure of Example 1 was repeated with the following ingredients,

| | |
|---|---|
| Morphine sulphate | 30 gm |
| Hydroxyethyl cellulose | 20 gm |
| Dioctyl sodium sulphosuccinate | 7.5 gm |
| Talc | 2.5 gm |
| Magnesium stearate | 1.25 gm |

| | |
|---|---|
| -continued | |
| Lactose | 63.75 gm |

This produced 1000 tablets weighing 125mg, each containing 30mg of morphine sulphate.

EXAMPLE 13

The procedure of Example 1 was repeated with the following ingredients,

| | |
|---|---|
| Codeine phosphate | 30 gm |
| Carboxymethyl cellulose | 30 gm |
| Dioctyl sodium sulphosuccinate (Ultrawet 40DS) | 7.5 gm |
| Talc | 2.5 gm |
| Magnesium stearate | 1.5 gm |
| Lactose | 53.75 gm |

This produced 1000 tablets weighing 125mg, each containing 30mg of codeine phosphate.

EXAMPLES 14 AND 15

The procedure of Example 4 was followed except that the dioctyl sodium sulphosuccinate was replaced by sodium dodecylsulphate (Example 14) and sodium dodecylbenzene sulphonate (Example 15).

Dissolution Studies

The rate of release of various compositions according to this invention were investigated using he USP Paddle Method (Propharmacopoeia no. 79) at 50rpm in 500 ml. on a pH gradient: pH 1.5 for the first hour, pH 4.5 for the second hour and pH 6.9 thereafter. The temperature was 37° C. samples were taken every hour.

Using this method, the dissolution rate of tablets prepared by Examples 3 to 11 above were determined. Results are given in the Tables below.

TABLE 1

Effect of varying the proportion of the hydroxypropyl Methylcellulose (HPMC) and the dioctyl sodium sulphosuccinate (DOS) on dissolution rates of metoclopramide HCl.

| | Example 3 HPMC, 18 mg DOS, 7.5 mg | Example 4 HPMC, 30 mg DOS, 5 mg | Example 5 HPMC, 42 mg DOS, 0 mg |
|---|---|---|---|
| 1 hr | 31% | 33% | 32% |
| 2 hr | 42% | 43% | 46% |
| 3 hr | 53% | 51% | 56% |
| 4 hr | 63% | 61% | 61% |
| 6 hr | 71% | 69% | 70% |
| 8 hr | 83% | 80% | 82% |

TABLE 2

Effect of changes in the amount of dioctyl sodium sulphosuccinate (DOS) with constant hydroxypropylmethylcellulose HPMC/on dissolution rates of metoclopramide HCl

| | Example 11 HPMC, 30 mg DOS, 0 mg | Example 10 HPMC, 30 mg DOS, 2 mg | Example 9 HPMC, 30 mg DOS, 4 mg | Example 8 HPMC, 30 mg DOS, 5 mg | Example 7 HPMC, 30 mg DOS, 6.25 mg | Example 6 HPMC, 30 mg DOS 12.5 mg |
|---|---|---|---|---|---|---|
| 1 hr | 41% | 38% | 36% | 33% | 26% | 18% |
| 2 hr | 62% | 55% | 46% | 43% | 38% | 25% |
| 3 hr | 69% | 62% | 54% | 51% | 49% | 32% |
| 4 hr | 75% | 70% | 62% | 61% | 56% | 38% |
| 5 hr | 91% | 83% | 77% | 69% | 66% | 51% |
| 6 hr | 97% | 93% | 89% | 80% | 75% | 63% |

TABLE 3

The effect of pH on the dissolution rate of metoclopramide HCl tablets prepared as described in Example 4

|      | pH gradient | pH 1.5 | pH 4.5 | pH 6.9 |
|------|-------------|--------|--------|--------|
| 1 hr | 33%         | 35%    | 30%    | 30%    |
| 2 hr | 43%         | 43%    | 44%    | 44%    |
| 3 hr | 51%         | 53%    | 50%    | 51%    |
| 4 hr | 61%         | 61%    | 56%    | 58%    |
| 5 hr | 69%         | 71%    | 67%    | 69%    |
| 6 hr | 80%         | 82%    | 79%    | 84%    |

TABLE 4

Dissolution of guinidine polygalaturonate tablets prepared as described in Example 2

|      | HPMC, 92 mg DOS, 4 mg |
|------|------------------------|
| 1 hr | 51.1                   |
| 2 hr | 61.4                   |
| 3 hr | 69.3                   |
| 4 hr | 75.1                   |
| 5 hr | 82.6                   |
| 6 hr | 86.6                   |

Clinical Studies

A comparative single dose pharmacokinetic study of two quinidine polygalaturonate preparations, namely quinidine polygalacturonate 412.5mg tablets prepared as described in Example 2 and controlled release quinidine polygalacturonate 412.5mg capsules (Cardioquine, Trade Mark) was carried out on 4 volunteers. Results are given in Table 5.

TABLE 5

| Time (hr) | TABLET Mean Plasma Level (ng/ml) | CAPSULE Mean Plasma Level (ng/ml) |
|-----------|----------------------------------|-----------------------------------|
| 0.17      | 0                                | 0                                 |
| 0.33      | 0.08                             | 0                                 |
| 0.50      | 0.24                             | 0.004                             |
| 0.75      | 0.41                             | 0.09                              |
| 1.0       | 0.42                             | 0.21                              |
| 1.5       | 0.46                             | 0.33                              |
| 2.0       | 0.53                             | 0.41                              |
| 2.5       | 0.57                             | 0.48                              |
| 3.0       | 0.57                             | 0.50                              |
| 4.0       | 0.62                             | 0.55                              |
| 5.0       | 0.72                             | 0.53                              |
| 6.0       | 0.67                             | 0.55                              |
| 8.0       | 0.59                             | 0.49                              |
| 10.0      | 0.54                             | 0.40                              |
| 12.0      | 0.43                             | 0.32                              |
| 24.0      | 0.23                             | 0.17                              |

A randomised, crossover, single dose comparative pharmacokinetic study of two quinidine polygalacturonate preparations, namely quinidine polygalacturonate 412.5mg tablets, prepared as described in Example 2, and controlled release quinidine polygalacturonate 412.5mg capsules (Cardioquine, Trade Mark), was carried out on 12 volunteers. Results are given in Tables 6, 7 and 8.

TABLE 6

| Time (hr) | TABLET Mean Plasma Level (ng/ml) | CAPSULE Mean Plasma Level (ng/ml) |
|-----------|----------------------------------|-----------------------------------|
| 0.25      | 0.042                            | 0.006                             |
| 0.5       | 0.22                             | 0.014                             |
| 0.75      | 0.37                             | 0.17                              |
| 1.0       | 0.47                             | 0.31                              |
| 1.5       | 0.55                             | 0.48                              |
| 2.0       | 0.64                             | 0.64                              |
| 2.5       | 0.66                             | 0.77                              |
| 3.0       | 0.69                             | 0.8                               |
| 4.0       | 0.71                             | 0.83                              |
| 5.0       | 0.67                             | 0.77                              |
| 6.0       | 0.62                             | 0.69                              |
| 8.0       | 0.51                             | 0.55                              |
| 10.0      | 0.43                             | 0.45                              |
| 12.0      | 0.35                             | 0.36                              |
| 24.0      | 0.13                             | 0.14                              |
| 30.0      | 0.08                             | 0.09                              |

TABLE 7

TABLETS (EXAMPLE 2)

|            | T MAX | C MAX | AUC 0-30 | AUC 0-INF | T½ ELIMIN. | MRT   |
|------------|-------|-------|----------|-----------|------------|-------|
| Subject 1  | 2     | 0.82  | 10.84    | 11.98     | 8.7        | 13.03 |
| Subject 2  | 3     | 1.05  | 12.39    | 12.95     | 6.26       | 10.55 |
| Subject 3  | 1     | 0.54  | 6.9      | 8.85      | 14.15      | 19.55 |
| Subject 4  | 2.5   | 0.94  | 9.2      | 10.17     | 8.92       | 12.68 |
| Subject 5  | 2     | 0.64  | 8.46     | 9.47      | 9.67       | 13.59 |
| Subject 6  | 4     | 0.81  | 11.7     | 14.68     | 12.92      | 18.94 |
| Subject 7  | 6     | 0.89  | 9.85     | 10.05     | 4.89       | 8.99  |
| Subject 8  | 3     | 0.88  | 12.83    | 15.22     | 10.72      | 16.25 |
| Subject 9  | 4     | 0.95  | 9.38     | 9.75      | 6.05       | 9.97  |
| Subject 10 | 5     | 0.65  | 6.74     | 7.16      | 6.81       | 11.25 |
| Subject 11 | 3     | 0.59  | 7.47     | 7.93      | 7.18       | 10.6  |
| Subject 12 | 2     | 0.82  | 11.61    | 12.95     | 8.84       | 13.51 |
| Average    | 3.13  | 0.8   | 9.78     | 10.93     | 8.76       | 13.24 |
| Standard Deviation | 1.42 | 0.16 | 2.12 | 2.6 | 2.8 | 3.42 |
| Subject 1  | 4     | 0.89  | 14.24    | 16.22     | 9.44       | 15    |
| Subject 2  | 4     | 1.04  | 12.91    | 15.01     | 10.96      | 15.23 |
| Subject 3  | 2.5   | 0.72  | 6.99     | 7.27      | 6.16       | 10.12 |
| Subject 4  | 5     | 0.77  | 10.82    | 12.89     | 11.17      | 16.68 |
| Subject 5  | 4     | 0.76  | 7.98     | 8.33      | 6.32       | 10.2  |
| Subject 6  | 3     | 0.67  | 9.4      | 9.97      | 6.56       | 11.57 |
| Subject 7  | 4     | 0.92  | 9.77     | 10.77     | 8.92       | 12.75 |
| Subject 8  | 5     | 0.87  | 11.13    | 12.24     | 8.24       | 13.17 |
| Subject 9  | 5     | 1.21  | 12.77    | 13.44     | 7.05       | 10.43 |
| Subject 10 | 4     | 0.66  | 7.04     | 7.9       | 9.94       | 13.36 |
| Subject 11 | 3     | 0.68  | 6.54     | 7.13      | 8.48       | 11.41 |
| Subject 12 | 2     | 1.03  | 14.17    | 15.16     | 8.75       | 13.63 |
| Average    | 3.79  | 0.85  | 10.31    | 11.41     | 8.5        | 12.8  |
| Standard Deviation | 0.99 | 0.17 | 2.81 | 3.33 | 1.72 | 2.13 |

While the invention has been described with respect to particular drugs, aionic surfactants and hydrophilic polymers, it is apparent that variations and modifications of the invention can be made without departing from the spirit or scope of the invention.

What is claimed is:

1. A solid, oral, controlled release pharmaceutical dosage form pharmaceutical composition comprising a matrix, formed of a pharmaceutically acceptable, water soluble, non-ionic, hydrophilic cellulose ether having a molecular weight of at least 50,000 having distributed therethorugh the complex drug of an acid addition salt of quaternary ammonium salt of an organic base drug and an anionic surfactant, the combined weight of said cellulose ether and anionic surfactant being between 10% and 60%, and said dosage form containing between 1 mg and 30 mg of said anionic surfactant, said complex being water soluble between pH 1.5 and 7.0, whereby the rate of drug release from said dosage form is independent of pH between said pH 1.5 and 7.0.

2. A composition according to claim 1 wherein the drug is an acid addition salt of an organic base.

3. A composition according to claim 2 wherein the drug is an acid addition salt of an organic amine.

4. A composition according to claim 1 wherein the drug is an acid addition salt of metoclopramide, codeine, ethylmorphine, morphine, dextromethorphan, quinidine, quinine, dihydrocodeine, hydromorphone, perphenazine, diltiazem, meptazinol or flupirtine.

5. A composition according to claim 1 wherein the drug is metoclopramide hydrochloride, codeine phosphate, ethylmorphine hydrochloride, morphine sulphate, dextromethorphan hydrobromide, quinidine polygalacturonate, quinine sulphate, dihydrocodeine tartrate, hydromorphone hydrochloride, perphenazine hydrochloride, dilitiazem hydrochloride, meptazinol hydrochloride or flupirtine maleate.

6. A composition according to claim 1 wherein the anionic surfactant is a sulphonate surfactant.

7. A composition according to claim 6 wherein the anionic surfactant is sulphosuccinate surfactant.

8. A composition according to claim 7 wherein the anionic surfactant is a dialkyl sulphosuccinate surfactant.

9. A composition according to claim 8 wherein the anionic surfactant is an alkali metal salt of dioctyl sulphosuccinate.

10. Method for the preparation of the solid, oral, controlled release pharmaceutical composition of claim 1, which comprises dissolving said anionic surfactant in a $C_1$–$C_6$ alkyl alcohol or an aqueous alcoholic solvent to form a solution thereof, mixing said water soluble, non-ionic cellulose ether having the molecular weight of at least 50,000 with the thus formed solution to form a homogeneous mixture thereof, granulating the thus formed homogenous mixture to form granules, drying the thus-formed granules, mixing said complex drug with said granules and compressing and shaping the thus formed mixture, whereby the drug complexes with the anionic surfactant to form a complex that is water soluble at pH between 1.5 and 7.0 and the cellulose ether forms a matrix through which the complex is distributed, whereby the rate of release of the drug from the composition is independent of the pH.

11. The solid, oral, controlled release pharmaceutical composition of claim 1 wherein said hydrophilic cellulose ether has a molecular weight of at least 75,000.

* * * * *